United States Patent [19]

Tamao et al.

[11] Patent Number: 6,143,834
[45] Date of Patent: Nov. 7, 2000

[54] OPTICALLY ACTIVE PHOSPHINE DERIVATIVE HAVING AT LEAST TWO VINYL GROUPS, POLYMER PRODUCED USING THE SAME AS MONOMER, AND TRANSITION METAL COMPLEXES OF THESE

[75] Inventors: Kyoko Tamao, Kyoto; Yohei Itoi, Shiga, both of Japan

[73] Assignee: Takasago International Corporation, Tokyo, Japan

[21] Appl. No.: 09/038,280

[22] Filed: Mar. 11, 1998

[30] Foreign Application Priority Data

Mar. 11, 1997 [JP] Japan ................................. 9-072817

[51] Int. Cl.[7] ........................ C08F 130/08; C08F 120/02; C08C 19/14
[52] U.S. Cl. ..................... 525/326.2; 525/330.2; 525/357
[58] Field of Search ............................ 525/326.6, 330.2, 525/357

[56] References Cited

PUBLICATIONS

Nozaki et.al. Highly enantioselective hydroformulation of olefins catalysed by Rhodium(I) complexes of new Chiral Phosphine–Phosphite ligands, J. Am. Chem. Soc., 1997, 119,4413–23.
Nozaki et.al. Asymmetric Hydroformulation of olefins in a highly cross–linked polymer matrix. J. Am. Chem. Soc., 1988, 120, 4051–2.
J. Org. Chem., 1986, vol. 51, pp. 4189–4195.
Tetrahedron: Asymmetry, vol. 6, pp. 2105–2108 (1995).
Tetrahedron: Asymmetry, vol. 6, pp. 2547–2555 (1995).
Tetrahedron: Asymmetry, vol. 6, pp. 2755–2766 (1995).
J. Org. Chem., 1990, vol. 55, pp. 304–310.
J. Org. Chem., 1990, vol. 55, pp. 6047–6049.
Journal of Molecular Catalysis, vol. 21, pp. 203–210 (1983).
J. C. S. Chem. Commun., 1982, pp. 473–474.
Chemtech, 1976, pp. 212–215.
J. Org. Chem., 1979, vol. 44, pp. 3152–3157.

Primary Examiner—David W. Wu
Assistant Examiner—Tanya Zalukaeva
Attorney, Agent, or Firm—Sughrue, Mion, Zinn, Macpeak & Seas, PLLC

[57] ABSTRACT

A transition metal complex of a polymer of 2'-diarylphosphino-1,1'-biphenylen-2-yloxy(6,6'-divinyl-1,1'-binaphthalene-2,2'-diyloxy)phosphine derivative is disclosed, which is represented by general formula (I):

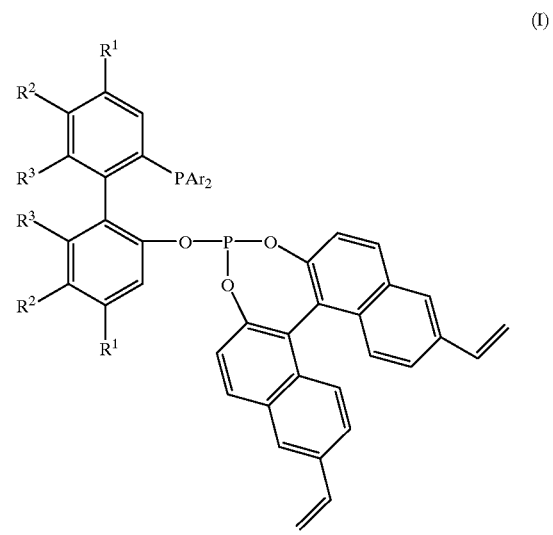

wherein Ar is an optionally substituted phenyl or naphthyl; $R^1$ and $R^2$ each independently is a hydrogen atom, a lower alkyl, a lower alkoxy, etc.; and $R^3$ is a lower alkyl, a lower alkoxy, etc.; provided that $R^2$ and $R^3$ may be bonded to each other to form a hydrocarbon ring, which may have one or more substituents selected from lower alkyl groups, halogen atoms, vinyl, etc. Also disclosed are a polymer having structural units derived from the phosphine derivative and a transition metal complex obtained by causing a transition metal compound to act on the phosphine derivative or the polymer. A novel polymer-supported ligand is provided which, when used as a catalyst for asymmetric syntheses, gives satisfactory results concerning catalytic activity, enantiomer excess, etc.

4 Claims, No Drawings

OPTICALLY ACTIVE PHOSPHINE DERIVATIVE HAVING AT LEAST TWO VINYL GROUPS, POLYMER PRODUCED USING THE SAME AS MONOMER, AND TRANSITION METAL COMPLEXES OF THESE

FIELD OF THE INVENTION

The present invention relates to a phosphine derivative, a polymer having structural units derived from the same as a polymer-forming base monomer, and complexes of these with a transition metal such as rhodium. This invention further relates to a method for obtaining an optically active compound in the presence of these transition metal complexes, which are utilizable as useful catalysts in asymmetric hydroformylation reactions.

BACKGROUND OF THE INVENTION

Many transition metal complexes have hitherto been used as catalysts for organic synthesis reactions. In particular, noble-metal complexes are extensively utilized, despite their expensiveness, since they are stable and easy to handle. Many investigations were made on syntheses using transition metal complexes including such noble-metal complexes as catalysts. As a result, many reports have been made on techniques making it possible to carry out organic synthesis reactions, including asymmetric reactions, which have been regarded as impossible with any conventional technique.

There are various types of optically active ligands for use in such asymmetric-synthesis catalysts. Among the ligands for use in asymmetric hydroformylation reactions using transition metal-phosphine complexes, one of the ligands having the highest degree of chiral recognition is 2-diphenylphosphino-1,1'-binaphthalen-2'-yloxy(1,1'-binaphthalene-2,2'-diyloxy)phosphine (hereinafter referred to simply as "BINAPHOS"). There are reports on the use of a rhodium complex containing BINAPHOS as a ligand in an olefin hydroformylation reaction, which is a reaction for forming asymmetric carbon-carbon bonds (see JP-A-6-263776 and JP-A-6-316560). (The term "JP-A" as used herein means an "unexamined published Japanese patent application".)

However, such expensive catalysts are unable to be recovered, or can be recovered only by a complicated separation method which is always accompanied by an undesirable loss. Furthermore, reuse of the recovered homogeneous catalysts is impossible and/or uneconomical. There has hence been a desire for a catalyst which can be easily recovered and reused and is capable of fully retaining its activity and, in particular, selectivity during repeated use.

With respect to synthetic chiral polymers, the application thereof to racemate separation media, reagents for asymmetric syntheses, catalysts, and the like is being extensively investigated. Rapid progress is being made recently in investigations on asymmetry recognition among the various functions of these chiral polymers. In particular, in the application thereof to stereoselective organic reactions, the chiral polymers can be used in a method different from those for general homogenous reaction systems because a specific reaction field constituted of the polymers is used.

Use of a polymeric reagent or polymeric catalyst in organic syntheses has an advantage that industrial processes can be improved because the reaction products can be easily separated and the reagent or catalyst can be reused.

For example, a report has been made on a process comprising reacting an optically active amino acid with 4-vinylbenzenesulfonyl chloride to obtain a chiral monomer, polymerizing the monomer with styrene and divinylbenzene to obtain a chiral polymer,

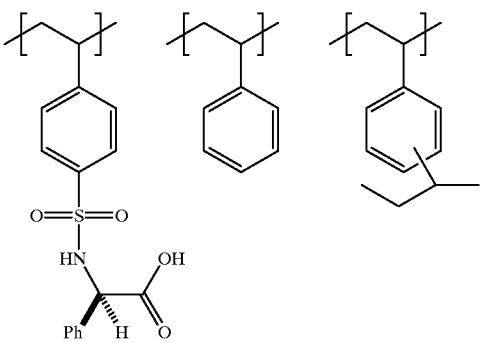

reacting this polymeric ligand with diborane to obtain a polymer-supported chiral oxaborolidinone, and using this compound as a Lewis acid catalyst to conduct the Diels-Alder reaction of cyclopentadiene with methacrolein (see S. Itsuno et al., *Tetrahedron: Asymmetry*, 1995, Vol. 6, p. 2547).

There also is a report on a method in which a Mn(II)-salen complex is polymerized

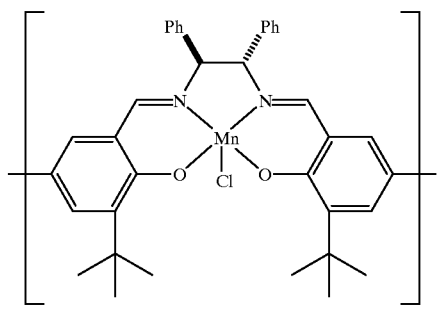

and the resultant polymer is used to conduct the asymmetric epoxidation reaction of an olefin (see S. Sivaram et al., *Tetrahedron: Asymmetry*, 1995, Vol. 6, p. 2105).

Furthermore, there is a report on a method which comprises copolymerizing optically active 2-p-styryl-4,5-bis[(dibenzophosphoryl)methyl]-1,3-dioxolane with styrene to obtain a chiral polymer,

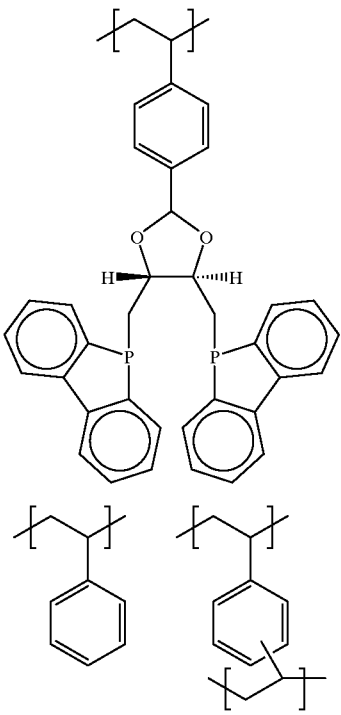

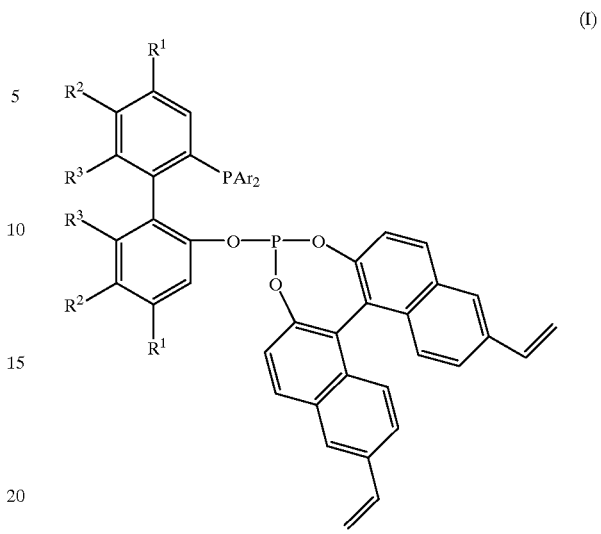

coordinating platinum chloride to this polymeric ligand, and using the resultant coordination compound to conduct the hydroformylation reaction of styrene in the presence of tin chloride (see J. K. Stille et al., *J. Org. Chem.*, 1986, Vol. 51, p. 4189).

However, all the prior art techniques have insufficient catalytic activity or result in an enantiomer excess lower than those in the case of reacting monomers. Any of those prior art techniques has not been put to industrial use.

SUMMARY OF THE INVENTION

As described above, there has been a desire for a polymer-supported ligand which, when used as a catalyst for asymmetric synthesis reactions, gives satisfactory results concerning catalytic activity, enantiomer excess, etc. An object of the present invention is to meet these requirements.

The present inventors have found that a polymeric ligand obtained by synthesizing a monomer which comprises a biphenyl framework having a diarylphosphino group at the 2'-position and a phosphite at the 2-position and in which the phosphite moiety has a naphthyl framework having two vinyl groups respectively at the 6- and 6'-positions, and then copolymerizing the monomer with a styrene derivative and a divinylbenzene derivative is an excellent ligand for use in asymmetric catalytic reactions. The present invention has been completed based on this finding.

The present invention provides a 2'-diarylphosphino-1,1'-biphenylen-2-yloxy(6,6'-divinyl-1,1'-binaphthalene-2,2'-diyloxy)phosphine derivative represented by the following general formula (I):

wherein Ar is an optionally substituted phenyl group or an optionally substituted naphthyl group; $R^1$ and $R^2$ each independently is a hydrogen atom, a lower alkyl group, a lower alkoxy group, a halogen atom, a halogen-substituted lower alkyl group, or a benzyloxy group; and $R^3$ is a lower alkyl group, a lower alkoxy group, a halogen atom, a halogen-substituted lower alkyl group, or a benzyloxy group; provided that $R^2$ and $R^3$ may be bonded to each other to form a hydrocarbon ring, which may have one or more substituents selected from lower alkyl groups, halogen atoms, lower alkoxy groups, halogenated lower alkyl groups, a benzyloxy group, and a vinyl group.

The present invention further provides an oligomer or polymer having structural units derived from a 2'-diarylphosphino-1,1'-biphenylen-2-yloxy(6,6'-divinyl-1,1'-binaphthalene-2,2'-diyloxy)phosphine derivative which are represented by the following general formula (III):

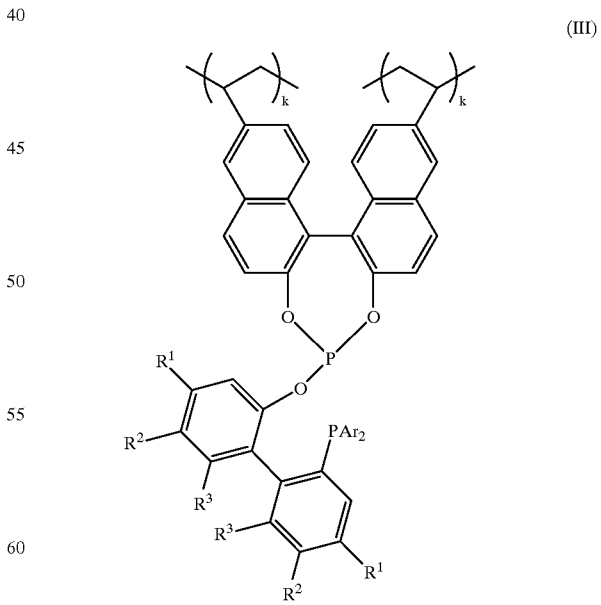

wherein $R^1$, $R^2$, $R^3$, and Ar have the same meanings as defined above; and k is an integer of 2 to 100.

The present invention furthermore provides transition metal complexes obtained by causing a transition metal compound to act on the compound represented by general formula (I) and on the polymer represented by general formula (III), respectively.

Another object of the present invention is to provide a process for producing an optically active α-methylaldehyde compound represented by the following general formula (B):

(B)

wherein $R^5$ is an alkyl group having 1 to 8 carbon atoms, an optionally substituted phenyl group, a naphthyl group, or an acetoxy group,
which comprises subjecting an olefin compound represented by the following general formula (A):

(A)

wherein $R^5$ has the same meaning as defined above, to asymmetric hydroformylation in the presence of any of the transition metal complexes.

DETAILED DESCRIPTION OF THE INVENTION

In compound (I) of the present invention, Ar is an optionally substituted phenyl group or an optionally substituted naphthyl group. Examples of the substituents thereof include lower alkyl groups having 1 to 4 carbon atoms, such as methyl, ethyl, propyl, isopropyl, n-butyl, t-butyl, and isobutyl, halogen atoms such as fluorine, chlorine, and bromine, lower alkoxy groups having 1 to 4 carbon atoms, such as methoxy, ethoxy, propoxy, and butoxy, halogenated lower alkyl groups such as trifluoromethyl and trichloromethyl, and benzyloxy. Preferred examples of Ar include phenyl, 4-tolyl, 4-methoxyphenyl, 3,5-xylyl, and naphthyl.

Examples of $R^1$ and $R^2$ include a hydrogen atom, lower alkyl groups having 1 to 4 carbon atoms, such as methyl, ethyl, propyl, isopropyl, n-butyl, t-butyl, and isobutyl, halogen atoms such as fluorine, chlorine, and bromine, lower alkoxy groups having 1 to 4 carbon atoms, such as methoxy, ethoxy, propoxy, and butoxy, halogenated lower alkyl groups such as trifluoromethyl and trichloromethyl, and benzyloxy.

Examples of $R^3$ include lower alkyl groups having 1 to 4 carbon atoms, such as methyl, ethyl, propyl, isopropyl, n-butyl, t-butyl, and isobutyl, halogen atoms such as fluorine, chlorine, and bromine, lower alkoxy groups having 1 to 4 carbon atoms, such as methoxy, ethoxy, propoxy, and butoxy, halogenated lower alkyl groups such as trifluoromethyl and trichloromethyl, and benzyloxy.

In the case where $R^2$ and $R^3$ are bonded to each other to form a hydrocarbon ring, examples of the hydrocarbon ring include benzene and cyclohexane rings which each may have one or more substituents. Examples of the substituents include lower alkyl groups having 1 to 4 carbon atoms, such as methyl, ethyl, propyl, isopropyl, n-butyl, t-butyl, and isobutyl, halogen atoms such as fluorine, chlorine, and bromine, lower alkoxy groups having 1 to 4 carbon atoms, such as methoxy, ethoxy, propoxy, and butoxy, halogenated lower alkyl groups such as trifluoromethyl and trichloromethyl, benzyloxy, and vinyl.

Compound (I) of the present invention is produced, for example, by a process shown by the following reaction scheme, in which the target compound is represented by general formula (I) wherein Ar is phenyl, $R^1$ is a hydrogen atom, and $R^2$ and $R^3$ are bonded to each other to form a hydrocarbon ring which is a benzene ring.

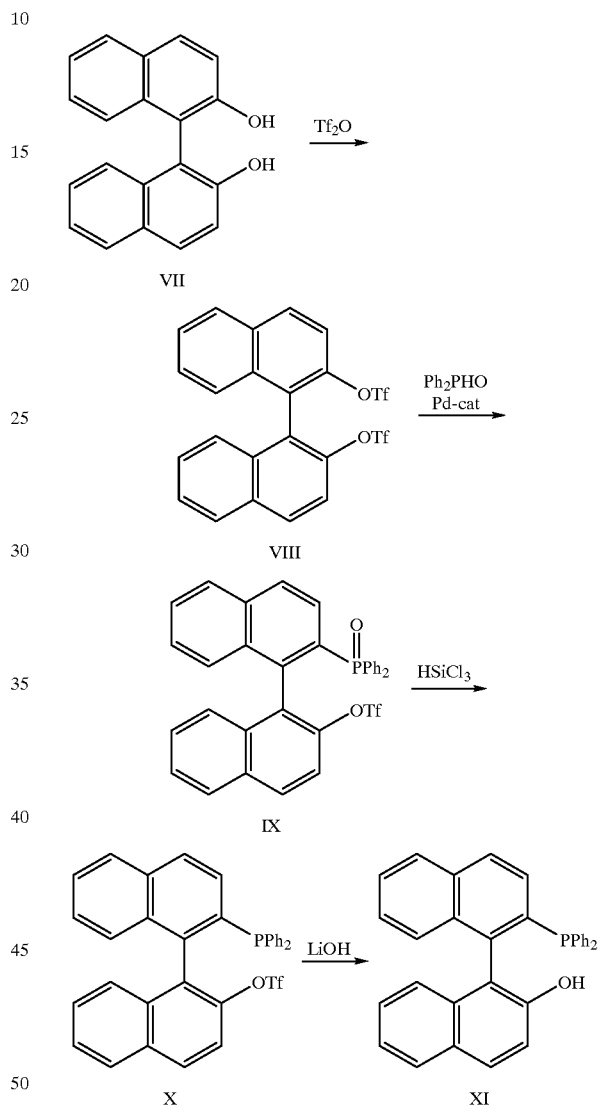

An optically active binaphthol (VII) as a starting material is reacted by a method described in the literature (M. Vondenhof and J. Mattay, *Tetrahedron Lett.*, 1990, Vol. 31, pp. 985–988; L. Kurz, G. Lee, D. Morgans, Jr., M. J. Waldyke, and T. Ward, *Tetrahedron Lett.*, 1990, Vol. 31, pp. 6321–6324) and by a method described in the literature (Y. Uozumi, A. Tanahashi, S.-Y. Lee, and T. Hayashi, *J. Org. Chem.*, 1993, Vol. 58, pp. 1945–1948). That is, the binaphthol (VII) is reacted with trifluoromethanesulfonic anhydride ($Tf_2O$) using pyridine in methylene chloride to convert compound (VII) to 2,2'-bis(trifluoromethanesulfonyloxy)-1, 1'-binaphthyl (VIII), which is reacted with diphenylphosphine oxide ($Ph_2PHO$) in the presence of a catalytic amount of a palladium-phosphine complex, whereby 2'-diphenylphosphinyl-2-trifluoromethanesulfonyloxy-1,1'- binaphthyl (IX) is synthesized. Compound (IX) is reduced with trichlorosilane (HSiCl₃) to obtain 2'-diphenylphosphino-2-trifluoromethanesulfonyloxy-1,1'-binaphthyl (X), which is hydrolyzed with lithium hydroxide (LiOH) to obtain 2'-diphenylphosphino-2-hydroxy-1,1'-binaphthyl (XI).

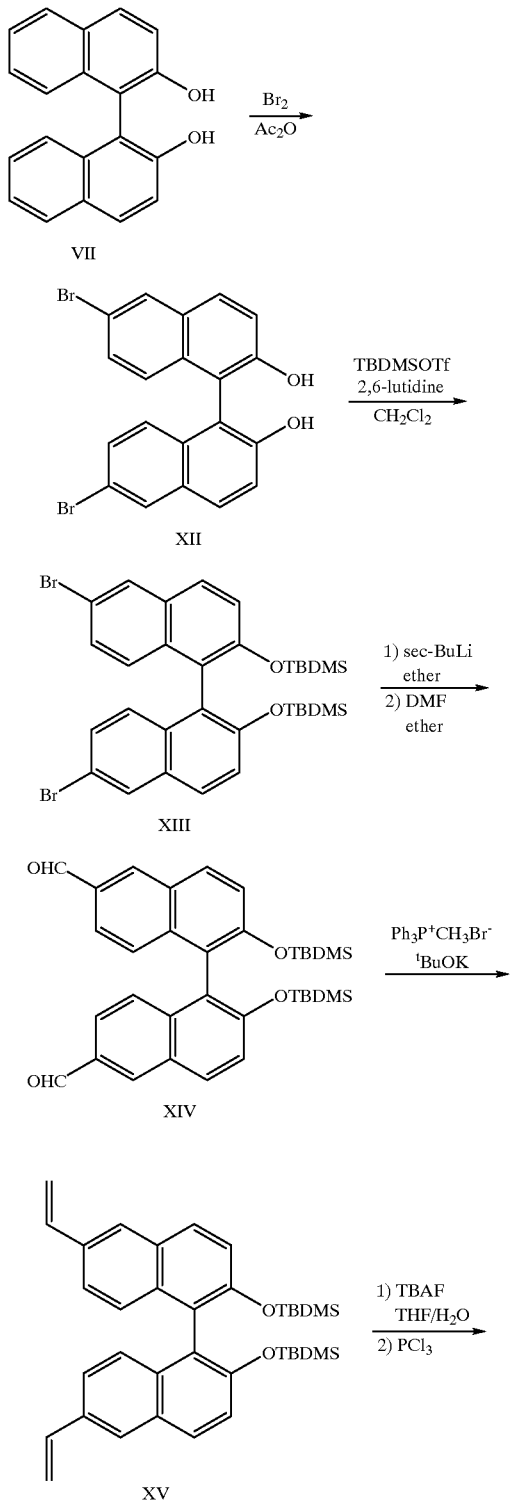

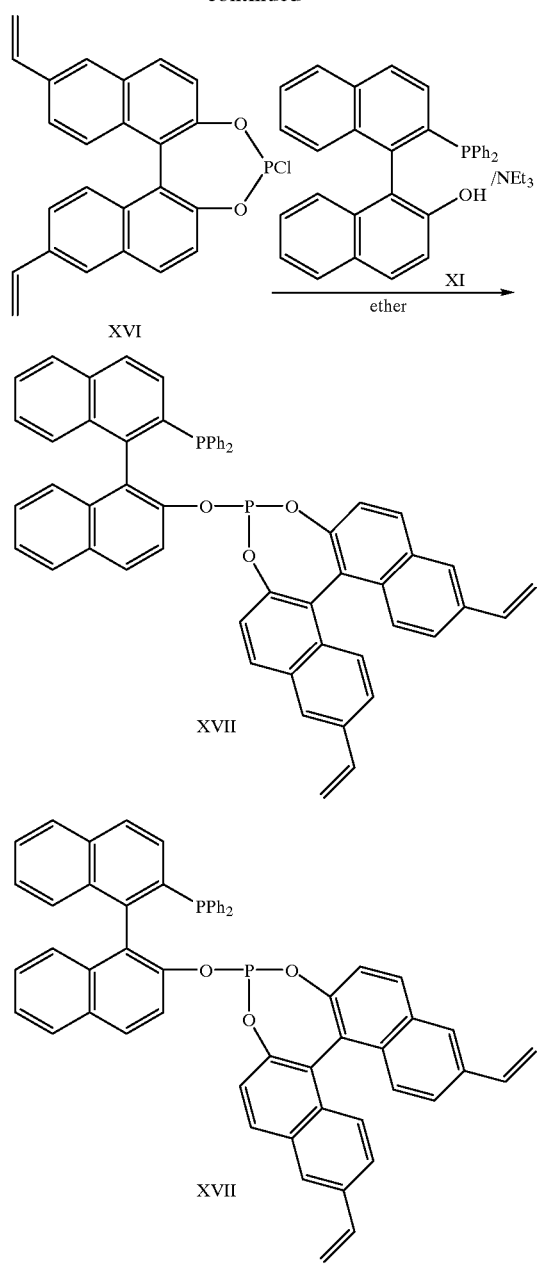

An optically active binaphthol (VII) is reacted with bromine in acetic anhydride to obtain 6,6'-dibromo-2,2'-dihydroxy-1,1'-binaphthyl (XII). The hydroxyl groups of compound (XII) are protected using tert-butyldimethylsilyl oxytriflate (TBDMSOTf) and 2,6-lutidine to obtain 6,6'-dibromo-2,2'-bis(tert-butyldimethylsilyloxy)-1,1'-binaphthyl (XIII). Compound (XIII) is converted to an anion form using sec-butyllithium (sec-BuLi), and dimethylformamide (DMF) is caused to act thereon to obtain 6,6'-diformyl-2,2'-bis(tert-butyldimethylsilyloxy)-1,1'-binaphthyl (XIV). Compound (XIV) is reacted with triphenylmethylphosphonium bromide (Ph₃P⁺CH₃Br⁻) and potassium t-butoxide (t-BuOK) to obtain 6,6'-divinyl-2,2'-bis(tert-butyldimethylsilyloxy)-1,1'-binaphthyl (XV). Compound (XV) is reacted with tetrabutylammonium fluoride (TBAF) for silyl removal to obtain 6,6'-divinyl-2,2'-dihydroxy-1,1'-binaphthyl, which is heated together with phosphorus trichloride to obtain 6,6'-divinyl-1,1'-binaphthalene-2,2'-dioxychlorophosphine (XVI). The 6,6'-divinyl-1,1'-binaphthalene-2,2'-dioxychlorophosphine (XVI) is reacted with 2'-diphenylphosphino-2-hydroxy-1,1'-binaphthyl (XI) in the presence of triethylamine (NEt₃) to obtain 2'-diphenylphosphino-1,1'-binaphthalen-2-yloxy(6,6'-divinyl-1,1'-binaphthalene-2,2'-diyloxy)phosphine (XVII).

The following is an example of processes for producing the compound (I) wherein Ar is phenyl, $R^1$ is a hydrogen atom, and $R^2$ and $R^3$ form a hydrocarbon ring which is a benzene ring having a vinyl group at the 6-position.

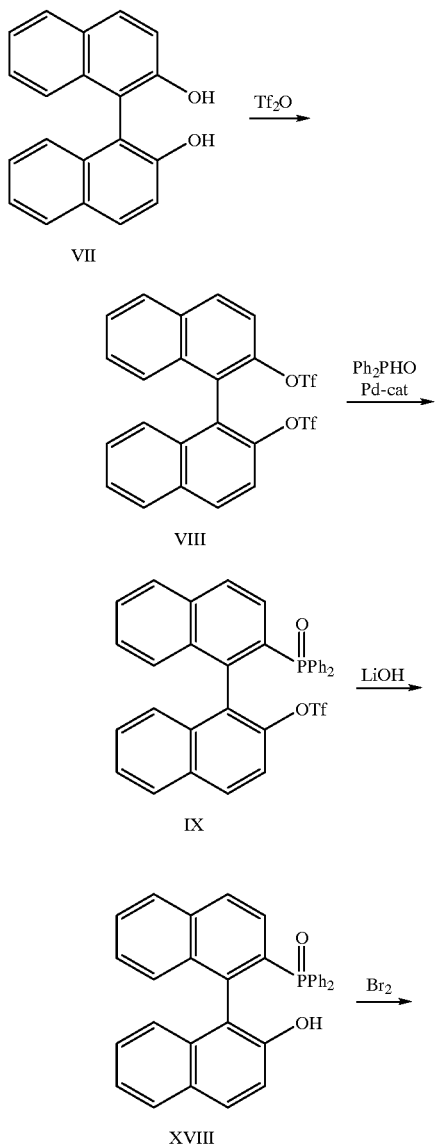

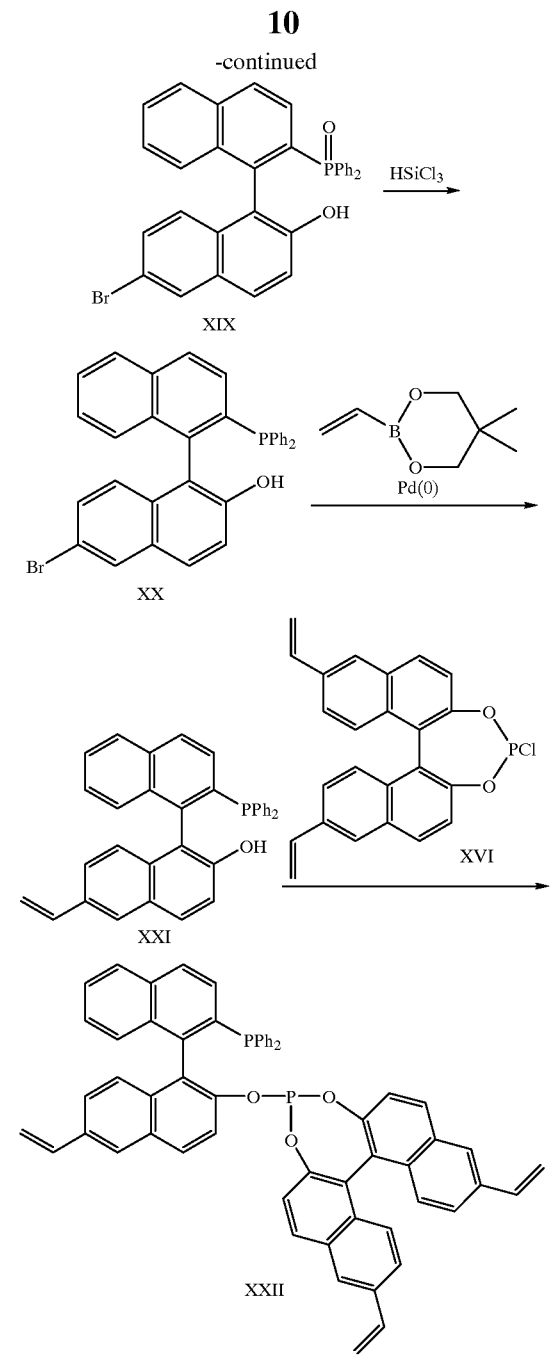

An optically active binaphthol (VII) as a starting material is reacted by a method described in the literature (M. Vondenhof and J. Mattay, *Tetrahedron Lett.*, 1990, Vol. 31, pp. 985–988; L. Kurz, G. Lee, D. Morgans, Jr., M. J. Waldyke, and T. Ward, *Tetrahedron Lett.*, 1990, Vol. 31, pp. 6321–6324) and by a method described in the literature (Y. Uozumi, A. Tanahashi, S.-Y. Lee, and T. Hayashi, *J. Org. Chem.*, 1993, Vol. 58, pp. 1945–1948). That is, the binaphthol (VII) is reacted with trifluoromethanesulfonic anhydride (Tf₂O) using pyridine in methylene chloride to convert compound (VII) to 2,2'-bis(trifluoromethanesulfonyloxy)-1,1'-binaphthyl (VIII), which is reacted with diphenylphosphine oxide ($Ph_2PHO$) in the presence of a catalytic amount of a palladium-phosphine complex, whereby 2'-diphenylphosphinyl-2-trifluoromethanesulfonyloxy-1,1'-binaphthyl (IX) can be synthesized. Compound (IX) is hydrolyzed with lithium hydroxide (LiOH) to obtain 2'-diphenylphosphinyl-2-hydroxy-1,1'-binaphthyl (XVIII), which is brominated in dioxane to obtain 2'-diphenylphosphinyl-2-hydroxy-6-bromo-1,1'-binaphthyl (XIX). Compound (XIX) is reduced with trichlorosilane ($HSiCl_3$) to obtain 2'-diphenylphosphino-2-hydroxy-6-bromo-1,1'-binaphthyl (XX), which is reacted with 2-vinyl-5,5-dimethyl-1,3-dioxa-2-borinane using a palladium catalyst by a method described in the literature (Y. Miyaura and A. Suzuki, *J. C. S. Chem. Commun.*, 1979, p. 866) to obtain 2'-diphenylphosphino-2-hydroxy-6-vinyl-1,1'-binaphthyl (XXI).

Finally, the 2'-diphenylphosphino-2-hydroxy-6-vinyl-1,1'-binaphthyl (XXI) is reacted with the 6,6'-divinyl-1,1'-binaphthalene-2,2'-dioxychlorophosphine (XVI) obtained above to thereby obtain 2'-diphenylphosphino-6-vinyl-1,1'-binaphthalen-2-yloxy(6,6'-divinyl-1,1'-binaphthalene-2,2'-diyloxy)phosphine (XXII) as the target compound.

The processes described above yield the compound represented by general formula (I) wherein Ar is phenyl, $R^1$ is a hydrogen atom, and $R^2$ and $R^3$ form a hydrocarbon ring which is a benzene ring and the compound represented by general formula (I) wherein Ar is phenyl, $R^1$ is a hydrogen atom, and $R^2$ and $R^3$ form a hydrocarbon ring which is a benzene ring having a vinyl group at the 6-position. However, these processes can be utilized also for obtaining other compounds represented by general formula (I).

Compound (I) of the present invention, obtained by the method described above, functions as a ligand to form a complex with a transition metal. Examples of the metal as a component of the complex include rhodium, iridium, palladium, platinum, cobalt, and nickel. Examples of the complex are given below. In the following formulae showing transition metal complexes, "L" represents compound (I) of the present invention, "cod" 1,5-cyclooctadiene, "nbd" norbornadiene, "Ph" phenyl, "Ac" acetyl, "OAc" acetoxy, and "acac" acetylacetonato. "L" represents (R)-2'-diphenylphosphino-1,1'-binaphthalen-2-yloxy[(S)-6,6'-divinyl-1,1'-binaphthalene-2,2'-diyloxy]phosphine as a typical example of compound (I) of the present invention.

Rhodium Complexes:

Examples of rhodium compounds used as complex precursors for forming rhodium complexes include the following.

$RhCl_3$, $RhBr_3$, $RhI_3$, $[Rh(cod)Cl]_2$, $[Rh(cod)Br]_2$, $[Rh(cod)I]_2$, $[Rh(nbd)Cl]_2$, $[Rh(nbd)Br]_2$, $[Rh(nbd)I]_2$, $[Rh(cod)(OAc)]_2$, $[Rh(nbd)(OAc)]_2$, $Rh(cod)(acac)$, $Rh(nbd)(acac)$, $Rh(CO)_2(acac)$, $[Rh(CO)_2Cl]_2$, $[Rh(CO)_2Br]_2$, $[Rh(CO)_2I]_2$, $[Rh(cod)_2]BF_4$, $[Rh(cod)_2]ClO_4$, $[Rh(cod)_2]PF_6$, $[Rh(cod)_2]BPh_4$, $[Rh(nbd)_2]BF_4$, $[Rh(nbd)_2]ClO_4$, $[Rh(nbd)_2]PF_6$, $[Rh(nbd)_2]BPh_4$ Such rhodium complexes may be produced, for example, by reacting dicarbonylacetylacetonatorhodium ($Rh(CO)_2(acac)$) with compound (I) of the present invention according to a method described in the literature (N. Sakai, S. Mano, K. Nozaki, H. Takaya, *J. Am. Chem. Soc.*, 1993, Vol. 115, p. 7033). Specific examples of the rhodium complexes obtained include the following.

Rh(acac)(L)
Rh(cod)Cl(L)
Rh(nbd)Cl(L)
Rh(cod)Br(L)
Rh(nbd)Br(L)
Rh(cod)(L)
Rh(nbd)(L)
Rh(OAc)(L)
RhH(CO)(L)
$[Rh(cod)(L)]ClO_4$
$[Rh(cod)(L)]BF_4$
$[Rh(cod)(L)]PF_6$
$[Rh(nbd)(L)]ClO_4$
$[Rh(nbd)(L)]BF_4$
$[Rh(nbd)(L)]PF_6$ Palladium Complexes:

Examples of palladium compounds used as complex precursors for forming palladium complexes include the following.

$PdCl_2$, $PdBr_2$, $PdI_2$, $[(\pi\text{-allyl})PdCl]_2$, $[(\pi\text{-allyl})PdBr]_2$, $[(\pi\text{-allyl})PdI]_2$, $[(\pi\text{-mathallyl})PdCl]_2$, $[(\pi\text{-methallyl})PdBr]_2$, $[(\pi\text{-methallyl})PdI]_2$, $PdCl_2(CH_3CN)_2$, $PdBr_2(CH_3CN)_2$, $PdI_2(CH_3CN)_2$, $PdCl_2(C_6H_5CN)_2$, $PdBr_2(C_6H_5CN)_2$, $PdI_2(C_6H_5CN)_2$, $PdCl_2(cod)$, $PdBr_2(cod)$, $PdI_2(cod)$, $PdCl_2(nbd)$, $PdBr_2(nbd)$, $PdI_2(nbd)$, $Pd(OAc)_2$, $Pd(acac)_2$ Such palladium complexes can be prepared by reacting L with π-allylpalladium chloride ($[(\pi\text{-allyl})PdCl]_2$) by a method described in the literature (Y. Uozumi and T. Hayashi, *J. Am. Chem. Soc.*, 1991, Vol. 113, p. 9887). Specific examples of the palladium complexes include the following.

$PdCl_2(L)$
(π-allyl)Pd(L)
$[Pd(L)]ClO_4$
$[Pd(L)]PF_6$
$[Pd(L)]BF_4$

Platinum Complexes:

Examples of platinum compounds used as complex precursors for forming platinum complexes include the following.

$PtCl_3$, $PtBr_3$, $PtI_3$, $PtCl_2(cod)$, $PtBr_2(cod)$, $PtI_2(cod)$, $PtCl_2(nbd)$, $PtBr_2(nbd)$, $PtI_2(nbd)$, $Pt(acac)_2$, $K_2PtCl_4$, $PtCl_2(CH_3CN)_2$, $PtBr_2(CH_3CN)_2$, $PtI_2(CH_3CN)_2$, $PtCl_2(PhCN)_2$, $PtBr_2(PhCN)_2$, $PtI_2(PhCN)_2$ Such platinum complexes can be prepared by mixing dibenzonitriledichloroplatinum ($PtCl_2(PhCN)_2$) with compound (I) in benzene with heating according to a method described in the literature (G. Consiglio, S. S. A. Nefkens, A. Borer, *Organometallics*, 1991, Vol. 10, p. 2046). A Lewis acid (e.g., $SnCl_2$) may be added if desired. Specific examples of the platinum complexes include the following.

$PtCl_2(L)$
$PtCl_2(SnCl_2)(L)$
$PtCl(SnCl_3)(L)$

Iridium Complexes:

Examples of iridium compounds used as complex precursors for forming iridium complexes include the following.

$IrCl_3$, $IrBr_3$, $IrI_3$, $[Ir(cod)Cl]_2$, $[Ir(cod)Br]_2$, $[Ir(cod)I]_2$, $[Ir(nbd)Cl]_2$, $[Ir(nbd)Br]_2$, $[Ir(nbd)I]_2$, $[Ir(cod)(OAc)]_2$, $[Ir(nbd)(OAc)]_2$, $Ir(cod)(acac)$, $Ir(nbd)(acac)$, $Ir(CO)_2(acac)$, $[Ir(CO)_2Cl]_2$, $[Ir(CO)_2Br]_2$, $[Ir(CO)_2I]_2$, $[Ir(cod)_2]BF_4$, $[Ir(cod)_2]ClO_4$, $[Ir(cod)_2]PF_6$, $[Ir(cod)_2]BPh_4$, $[Ir(nbd)_2]BF_4$, $[Ir(nbd)_2]ClO_4$, $[Ir(nbd)_2]PF_6$, $[Ir(nbd)_2]BPh_4$ Such iridium complexes can be prepared by mixing L with [(1,5-cyclooctadiene)(acetonitrile)iridium] tetrafluoroborate ($[Ir(cod)(CH_3CN)_2]BF_4$) in tetrahydrofuran according to a method described in the literature (K.

Mashima, T. Akutagawa, X. Zhang, T. Taketomi, H. Kumobayashi, S. Akutagawa, *J. Organomet. Chem.*, 1992, Vol. 428, p. 213). Specific examples of the iridium complexes include the following.

[Ir(cod)(L)]ClO$_4$

[Ir(cod)(L)]PF$_6$

[Ir(cod)(L)]BF$_4$

[Ir(nbd)(L)]ClO$_4$

[Ir(nbd)(L)]PF$_6$

[Ir(nbd)(L)]BF$_4$

Ir(cod)(L)Cl

Ir(nbd)(L)Cl

Ir(cod)(L)Br

Ir(nbd)(L)Br

Ir(cod)(L)

Ir(nbd)(L)

Ir(OAc)(L)

The present invention furthermore provides an oligomer or polymer produced by polymerizing compound (I) of the present invention. The oligomer or polymer has structural units derived from a 2'-diarylphosphino-1,1'-biphenylen-2-yloxy(6,6'-divinyl-1,1'-binaphthalene-2,2'-diyloxy)phosphine derivative which are represented by the following general formula (III):

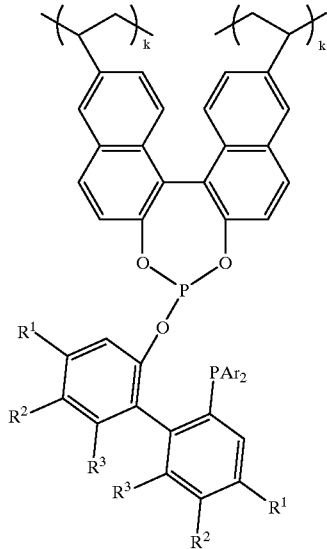

(III)

wherein R$^1$, R$^2$, R$^3$, and Ar have the same meanings as defined above; and k is an integer of 2 to 100.

The polymer especially preferably has structural units derived from compounds which units are represented by the following general formulae (III), (IV), and (V):

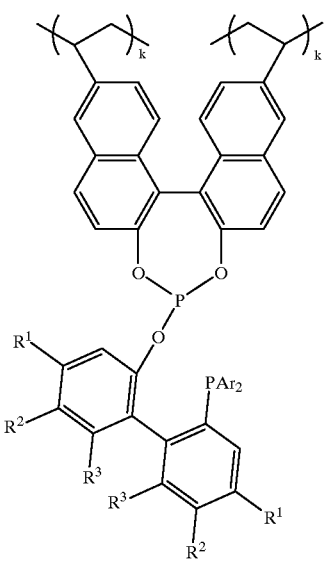

(III)

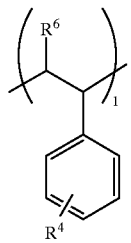

(IV)

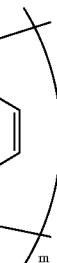

(V)

wherein R$^1$, R$^2$, R$^3$, and Ar have the same meanings as defined above; R$^4$ is a hydrogen atom, a lower alkyl group, a lower alkoxy group, or a halogen atom; R$^6$ is a hydrogen atom or a methyl group; k is an integer of 2 to 100; and l and m each is an integer of 0 to 1,000; provided that (k+l+m) is from 10 to 1,000.

The polymer is preferably formed from monomers comprising compound (III) and at least one member selected from the group consisting of the styrene derivative (IV) and the divinylbenzene derivative (V).

Examples of R$^4$ in the styrene derivative monomer (IV) according to the present invention include a hydrogen atom, lower alkyl groups having 1 to 4 carbon atoms, such as methyl, ethyl, isopropyl, n-butyl, and t-butyl, lower alkoxy groups having 1 to 4 carbon atoms, such as methoxy, ethoxy, propoxy, and butoxy, and halogen atoms such as chlorine and bromine.

The polymer (III) of the present invention can be produced using a known polymerization method, e.g., solution polymerization or suspension polymerization.

This polymerization reaction is conducted as follows. The phosphine derivative (I) and the styrene derivative and/or divinylbenzene derivative are suspended or dissolved in an aqueous poly(vinyl alcohol) solution, a halogenated hydrocarbon, e.g., chloroform, or a hydrocarbon, e.g., toluene, and the resultant suspension or solution is introduced into a reactor in an inert gas atmosphere, e.g., nitrogen or argon. An azo compound, e.g., 2,2'-azobis(2,4-dimethylvaleronitrile) or azobisisobutyronitrile, or a peroxide is added thereto as a free-radical initiator, and the reaction mixture is reacted at ordinary pressure and a temperature of 60 to 100° C. for 1 hour to 2 days to thereby conduct the polymerization.

In producing the polymer of the present invention, the proportions of compounds (III), (IV), and (V) mixed together are represented by the ratio between k, l, and m, i.e., molar ratio. Specifically, k:l:m is (2 to 100):(0 to 1,000):(0 to 1,000). Preferably, k:l:m is (1 to 100):(100 to 1,000):(0 to 1,000).

In the polymer of the present invention, the degrees of polymerization of compounds (III), (IV), and (V) are shown by k, l, and m, respectively, and (k+l+m) is in the range of from 10 to 1,000.

The polymer (III) of the present invention thus obtained functions as a ligand to form a complex with a transition metal. Examples of the metal as a component of the complex include rhodium, iridium, palladium, platinum, cobalt, and nickel. Examples of the complex are given below. In the following formulae showing transition metal complexes, "L" represents the monomer of compound (III) of the present invention, "cod" 1,5-cyclooctadiene, "nbd" norbornadiene, "Ph" phenyl, "Ac" acetyl, "OAc" acetoxy, and "acac" acetylacetonato. "L" represents (R)-2'-diphenylphosphino-1,1'-binaphthalen-2-yloxy[(S)-6,6'-divinyl-1,1'-binaphthalene-2,2'-diyloxy]phosphine monomer as a typical example of compound (III) of the present invention. Furthermore, "k" is an integer of 2 to 100.

Rhodium Complexes:

Examples of rhodium compounds used as complex precursors for forming rhodium complexes include the following.

$RhCl_3$, $RhBr_3$, $RhI_3$, $[Rh(cod)Cl]_2$, $[Rh(cod)Br]_2$, $[Rh(cod)I]_2$, $[Rh(nbd)Cl]_2$, $[Rh(nbd)Br]_2$, $[Rh(nbd)I]_2$, $[Rh(cod)(OAc)]_2$, $[Rh(nbd)(OAc)]_2$, $Rh(cod)(acac)$, $Rh(nbd)(acac)$, $Rh(CO)_2(acac)$, $[Rh(CO)_2Cl]_2$, $[Rh(CO)_2Br]_2$, $[Rh(CO)_2I]_2$, $[Rh(cod)_2]BF_4$, $[Rh(cod)_2]ClO_4$, $[Rh(cod)_2]PF_6$, $[Rh(cod)_2]BPh_4$, $[Rh(nbd)_2]BF_4$, $[Rh(nbd)_2]ClO_4$, $[Rh(nbd)_2]PF_6$, $[Rh(nbd)_2]BPh_4$ Such rhodium complexes may be produced, for example, by reacting dicarbonylacetylacetonatorhodium ($Rh(CO)_2(acac)$) with compound (III) of the present invention according to a method described in the literature (N. Sakai, S. Mano, K. Nozaki, H. Takaya, *J. Am. Chem. Soc.*, 1993, Vol. 115, p. 7033). Specific examples of the rhodium complexes obtained include the following.

$[Rh(acac)]_k(L)$
$[Rh(cod)Cl]_k(L)$
$[Rh(nbd)Cl]_k(L)$
$[Rh(cod)Br]_k(L)$
$[Rh(nbd)Br]_k(L)$
$[Rh(cod)]_k(L)$
$[Rh(nbd)]_k(L)$
$[Rh(OAc)]_k(L)$
$[RhH(CO)_2]_k(L)$
$[Rh_k(cod)_k(L)](ClO_4)_k$
$[Rh_k(cod)_k(L)](BF_4)_k$
$[Rh_k(cod)_k(L)](PF_6)_k$
$[Rh_k(nbd)_k(L)](ClO_4)_k$
$[Rh_k(nbd)_k(L)](BF_4)_k$
$[Rh_k(nbd)_k(L)](PF_6)_k$ Palladium Complexes:

Examples of palladium compounds used as complex precursors for forming palladium complexes include the following.

$PdCl_2$, $PdBr_2$, $PdI_2$, $[(\pi\text{-allyl})PdCl]_2$, $[(\pi\text{-allyl})PdBr]_2$, $[(\pi\text{-allyl})PdI]_2$, $[(\pi\text{-mathallyl})PdCl]_2$, $[(\pi\text{-methallyl})PdBr]_2$, $[(\pi\text{-methallyl})PdI]_2$, $PdCl_2(CH_3CN)_2$, $PdBr_2(CH_3CN)_2$, $PdI_2(CH_3CN)_2$, $PdCl_2(C_6H_5CN)_2$, $PdBr_2(C_6H_5CN)_2$, $PdI_2(C_6H_5CN)_2$, $PdCl_2(cod)$, $PdBr_2(cod)$, $PdI_2(cod)$, $PdCl_2(nbd)$, $PdBr_2(nbd)$, $PdI_2(nbd)$, $Pd(OAc)_2$, $Pd(acac)_2$ Such palladium complexes can be prepared by reacting L with π-allylpalladium chloride ($[(\pi\text{-allyl})PdCl]_2$) by a method described in the literature (Y. Uozumi and T. Hayashi, *J. Am. Chem. Soc.*, 1991, Vol. 113, p. 9887). Specific examples of the palladium complexes include the following.

$(PdCl_2)_k(L)$
$[(\pi\text{-allyl})Pd]_k(L)$
$[Pd_k(L)](ClO_4)_k$
$[Pd_k(L)](PF_6)_k$
$[Pd_k(L)](BF_4)_k$ Platinum Complexes:

Examples of platinum compounds used as complex precursors for forming platinum complexes include the following.

$PtCl_2$, $PtBr_2$, $PtI_2$, $PtCl_2(cod)$, $PtBr_2(cod)$, $PtI_2(cod)$, $PtCl_2(nbd)$, $PtBr_2(nbd)$, $PtI_2(nbd)$, $Pt(acac)_2$, $K_2PtCl_4$, $PtCl_2(CH_3CN)_2$, $PtBr_2(CH_3CN)_2$, $PtI_2(CH_3CN)_2$, $PtCl_2(PhCN)_2$, $PtBr_2(PhCN)_2$, $PtI_2(PhCN)_2$ Such platinum complexes can be prepared by mixing dibenzonitriledichloroplatinum ($PtCl_2(PhCN)_2$) with compound (III) in benzene with heating according to a method described in the literature (G. Consiglio, S. S. A. Nefkens, A. Borer, *Organometallics*, 1991, Vol. 10, p. 2046). A Lewis acid (e.g., $SnCl_2$) may be added if desired. Specific examples of the platinum complexes include the following.

$[PtCl_2]_k(L)$
$[PtCl_2(SnCl_2)]_k(L)$
$[PtCl(SnCl_3)]_k(L)$

Iridium Complexes:

Examples of iridium compounds used as complex precursors for forming iridium complexes include the following.

$IrCl_3$, $IrBr_3$, $IrI_3$, $[Ir(cod)Cl]_2$, $[Ir(cod)Br]_2$, $[Ir(cod)I]_2$, $[Ir(nbd)Cl]_2$, $[Ir(nbd)Br]_2$, $[Ir(nbd)I]_2$, $[Ir(cod)(OAc)]_2$, $[Ir(nbd)(OAc)]_2$, $Ir(cod)(acac)$, $Ir(nbd)(acac)$, $Ir(CO)_2(acac)$, $[Ir(CO)_2Cl]_2$, $[Ir(CO)_2Br]_2$, $[Ir(CO)_2I]_2$, $[Ir(cod)_2]BF_4$, $[Ir(cod)_2]ClO_4$, $[Ir(cod)_2]PF_6$, $[Ir(cod)_2]BPh_4$, $[Ir(nbd)_2]BF_4$, $[Ir(nbd)_2]ClO_4$, $[Ir(nbd)_2]PF_6$, $[Ir(nbd)_2]BPh_4$ Such iridium complexes can be prepared by mixing L with [(1,5-octadiene)(acetonitrile)iridium] tetrafluoroborate ($[Ir(cod)(CH_3CN)_2]BF_4$) in tetrahydrofuran according to a method described in the literature (K. Mashima, T. Akutagawa, X. Zhang, T. Taketomi, H. Kumobayashi, S. Akutagawa, *J. Organomet. Chem.*, 1992, Vol. 428, p. 213). Specific examples of the iridium complexes include the following.

$[Ir_k(cod)_k(L)](ClO_4)_k$
$[Ir_k(cod)_k(L)](PF_6)_k$
$[Ir_k(cod)_k(L)](BF_4)_k$
$[Ir_k(nbd)_k(L)](ClO_4)_k$

[Ir$_k$(nbd)$_k$(L)](PF$_6$)$_k$
[Ir$_k$(nbd)$_k$(L)](BF$_4$)$_k$
[Ir(cod)]$_k$(L)Cl$_k$
[Ir(nbd)]$_k$(L)Cl$_k$
[Ir(cod)]$_k$(L)Br$_k$
[Ir(nbd)]$_k$(L)Br$_k$
[Ir(cod)]$_k$(L)
[Ir(nbd)]$_k$(L)
[Ir(OAc)]$_k$(L)

The transition metal complex thus obtained from compound (I) of the present invention or the polymer comprising structural units (III) or comprising structural units (III), (IV), and (V) and from a transition metal compound can be utilized as a catalyst for asymmetric syntheses. For example, the complex can be used as a catalyst for a process in which an olefin compound (A) shown below is reacted in a pressurized atmosphere of carbon monoxide and hydrogen to produce an optically active α-methylaldehyde compound (B) (hydroformylation reaction):

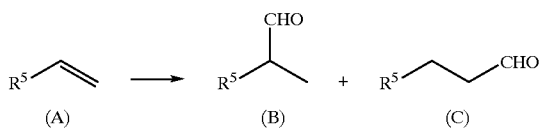

wherein R$^5$ represents an alkyl group having 1 to 8 carbon atoms, an optionally substituted phenyl group, a naphthyl group, or an acetoxy group.

Namely, a transition metal complex containing as a ligand the phosphine derivative (I) or the oligomer or polymer (III) which each has been selected with respect to (R),(S) isomer or (S),(R) isomer is used as a catalyst in the above reaction, whereby the optically active target compound having the desired absolute configuration can be synthesized. Examples of the group R$^5$ in the olefin compound (A) used as a starting compound in the above reaction include alkyl groups such as methyl, ethyl, propyl, isopropyl, n-butyl, t-butyl, pentyl, hexyl, heptyl, and octyl, optionally substituted phenyl groups such as phenyl, 2-, 3-, or 4-methoxyphenyl, 2-, 3-, or 4-chlorophenyl, 2-, 3-, or 4-fluorophenyl, 2-, 3-, or 4-trifluoromethylphenyl, and 2-, 3-, or 4-tolyl, and other groups including naphthyl, acetoxy, and phthaloyl.

On the other hand, a solvent such as, e.g., benzene, toluene, xylene, tetrahydrofuran, methylene chloride, 1,2-dichloroethane, or acetone can be used for the reaction.

The amount of the catalyst used in the above reaction to the substrate is about from 0.01 to 10 mol %, preferably about from 0.05 to 5 mol %, in terms of the transition metal compound (II) or the transition metal compound comprising structural units (VI) or comprising structural units (VI), (IV), and (V).

The reaction is usually carried out by maintaining the reaction mixture at a temperature of about from 10 to 100° C., preferably about from 20 to 50° C., for about from 10 minutes to 30 hours in an atmosphere of carbon monoxide and hydrogen having a pressure of about from 2 to 120 atm. However, these conditions can be suitably changed according to the amounts of the reactants used, etc.

After the reaction, the polymeric transition metal compound of the present invention comprising structural units (VI) or structural units (VI), (IV), and (V) can be virtually completely separated from the reaction mixture by a simple method, e.g., centrifuging or filtration. The catalyst thus recovered can be reused.

The present invention will be explained below in more detail by reference to Examples, but the invention should not be construed as being limited thereby in any way.

The following apparatuses were used for property determination in the Examples.

$^1$H NMR: JMN-EX-270 (270 MHz), manufactured by JEOL, Japan $^{31}$P NMR: JMN-EX-270 (109 MHz), manufactured by JEOL Angle of rotation: DIP-360, manufactured by JASCO Corp., Japan GLC: GC-15A, manufactured by Shimadzu Corp., Japan MASS: QP-1000, manufactured by Shimadzu Corp.

EXAMPLE 1

Synthesis of (R)-2'-diphenylphosphino-1,1'-binaphthalen-2-yloxy[(S)-6,6'-divinyl-1,1'-binaphthalene-2,2'-diyloxy]phosphine (1) Synthesis of (R)-2,2'-bis[trifluoromethanesulfonyloxy]-1,1'-binaphthyl In 181 ml of methylene chloride were dissolved 36.2 g (127 mmol) of (R)-binaphthol and 25.2 g (319 mmol) of pyridine. This solution was cooled to 0° C. Thereto was added dropwise 76.5 ml (271 mmol) of trifluoromethanesulfonic anhydride. Thereafter, the resultant mixture was stirred at room temperature for 18 hours, and 200 ml of 2 N hydrochloric acid was then added to the reaction mixture to wash the same. The organic layer was washed with water and a sodium chloride solution, and the solvent was then distilled off, whereby 69.3 g of a crude reaction product was obtained. The crude product was recrystallized from 280 ml of hexane to obtain 64.1 g (yield, 92%) of the target compound.

$^1$H NMR (CDCl$_3$) δ7.25–8.15 (m, aromatic)

(2) Synthesis of (R)-2'-diphenylphosphinyl-2-trifluoromethanesulfonyloxy-1,1'-binaphthyl In 100 ml of dimethyl sulfoxide (DMSO) were dissolved 11 g (20 mmol) of (R)-2,2'-bis[trifluoromethanesulfonyloxy]-1,1'-binaphthyl, 0.225 g (50 mol %) of palladium acetate, and 0.43 g (50 mol %) of 1,3-bis(diphenylphosphino)propane. This solution was stirred at room temperature for 1.5 hours. Thereto was added a solution prepared by dissolving 8.08 g (40 mmol) of diphenylphosphine oxide and 20 ml of diisopropylethylamine in 100 ml of dimethyl sulfoxide (DMSO). The resultant mixture was stirred at 100° C. for 12 hours. After the reaction mixture was cooled to room temperature, 75 ml of methylene chloride was added thereto. This solution was cooled in an ice bath, and 100 ml of 2 N hydrochloric acid was gradually added dropwise thereto. The resultant mixture was stirred at room temperature for 30 minutes and then subjected to liquid separation. The aqueous layer was extracted with methylene chloride. The resultant organic layer was collected, washed with water, and then dried with anhydrous magnesium sulfate. The dried organic layer was concentrated for solvent removal, and the residue was purified by silica gel column chromatography (hexane/ethyl acetate=4/1 to 1/4 by volume). As a result, 11.5 g (yield, 96%) of the target compound was obtained as yellowish white crystals.

[α]$_D^{24}$ 44.45° (c 0.50, CHCl$_3$)

$^1$H NMR (CDCl$_3$) δ7.0–8.01 (m, aromatic)

$^{31}$P NMR (CDCl$_3$) δ28.73 (s)

(3) Synthesis of (R)-2'-diphenylphosphino-2-trifluoromethanesulfonyloxy-1,1'-binaphthyl In 22 ml of xylene was dissolved 400 mg (0.664 mmol) of (R)-2'-diphenylphosphinyl-2-trifluoromethanesulfonyloxy-1,1'-binaphthyl. Thereto were added 1.20 g (12 mmol) of triethylamine and 1.62 g (12 mmol) of trichlorosilane. The resultant mixture was stirred at 120° C. for 17 hours. After the reaction mixture was cooled to room temperature, 4.4 ml of 35% sodium hydroxide solution was carefully added thereto. This mixture was stirred for further two hours and then subjected to liquid separation. The organic layer was washed twice with 30 ml of saturated sodium chloride solution and then dried with anhydrous magnesium sulfate. The solvent was distilled off at a reduced pressure to thereby obtain the target compound as a crude reaction product. This unpurified compound as such was subjected to the following reaction.

(4) Synthesis of (R)-2'-diphenylphosphino-2-hydroxy-1,1'-binaphthyl

The (R)-2'-diphenylphosphinyl-2-trifluoromethanesulfonyloxy-1,1'-binaphthyl obtained above was dissolved in 7 ml of tetrahydrofuran. Thereto were added 335 mg (8.0 mmol) of lithium hydroxide monohydrate (LiOH.$H_2$O) and purified water (2.4 ml). After this mixture was stirred for 15 hours, the tetrahydrofuran was distilled off at a reduced pressure. To the residue were added ether (10 ml) and 5% hydrochloric acid (10 ml). The resultant mixture was stirred and then subjected to liquid separation. Thereafter, the organic layer was washed with water twice and then dried with anhydrous magnesium sulfate. The dried organic layer was concentrated to distill off the solvent, and the residue was purified by silica gel column chromatography (hexane/ethyl acetate=5/1 by volume). As a result, 153 mg of the target compound was obtained (yield based on (R)-2'-diphenylphosphinyl-2-trifluoromethanesulfonyloxy-1,1'-binaphthyl, 51%).

(5) Synthesis of (S)-6,6'-dibromo-2,2'-dihydroxy-1,1'-binaphthyl

In 200 ml of glacial acetic acid was dissolved 28.63 g (0.1 mol) of (S)-binaphthol. After this solution was heated to 60° C., 32 g (0.2 mol) of bromine and 50 ml of glacial acetic acid were added thereto dropwise. The resultant mixture was stirred at that temperature for 30 minutes and then at room temperature overnight. The solvent was distilled off at a reduced pressure. As a result, 44.61 g of the target compound was obtained.

(6) Synthesis of (S)-6,6'-dibromo-2,2'-bis(tert-butyldimethylsilyloxy)-1,1'-binaphthyl In 20 ml of methylene chloride were dissolved 2.42 g (4.86 mmol) of (S)-6,6'-dibromo-2,2'-dihydroxy-1,1'-binaphthyl, 2.4 ml (10.5 mmol) of tert-butyldimethylsilyl triflate, and 1.2 ml (10.3 mmol) of 2,6-lutidine. This solution was stirred at room temperature for 7 hours. Saturated aqueous sodium bicarbonate solution was added thereto, and the resultant mixture was subjected to liquid separation. Thereafter, the organic layer was washed with saturated sodium chloride solution and water and then dried with anhydrous magnesium sulfate. The solvent was distilled off at a reduced pressure, and the residue was purified by silica gel column chromatography (hexane/ethyl acetate=5/1 by volume). As a result, 3.19 g (yield, 91%) of the target compound was obtained.

$^1$H NMR (CDCl$_3$) δ−0.16 (s, 6H), 0.02 (s, 6H), 0.48 (s, 18H), 7.02 (d, J=8.91 Hz, 2H), 7.18 (d, J=8.91 Hz, 2H), 7.27 (dd, J=1.98, 8.91 Hz, 2H), 7.72 (d, J=8.91 Hz, 2H), 7.97 (d, J=1.98 Hz, 2H)

(7) Synthesis of (S)-6,6'-diformyl-2,2'-bis(tert-butyldimethylsilyloxy)-1,1'-binaphthyl Into an 80-ml Schlenk tube was introduced 2.19 g (3.26 mmol) of (S)-6,6'-dibromo-2,2'-bis(tert-butyldimethylsilyloxy)-1,1'-binaphthyl, followed by 12 ml of ether. Thereto was added dropwise sec-butyllithium (7.76 mmol, hexane solution). The resultant mixture was stirred at 0° C. for 2 hours. To this solution maintained at that temperature were added 0.6 ml (7.76 mmol) of dimethylformamide and 5 ml of ether. After the resultant mixture was stirred for 12 hours, 3 N HCl was added thereto to terminate the reaction. The reaction mixture was neutralized with saturated aqueous sodium bicarbonate solution and then subjected to liquid separation. The organic layer was washed with saturated sodium chloride solution and then dried with anhydrous magnesium sulfate. The dried organic layer was concentrated for solvent removal, and the residue was purified by silica gel column chromatography (hexane/ethyl acetate=4/1 by volume). As a result, 1.34 g (yield, 74%) of the target compound was obtained.

$^1$H NMR (CDCl$_3$) δ−0.08 (s, 6H), 0.06 (s, 6H), 0.43 (s, 18H), 7.25–7.30 (m, 2H), 7.69 (dd, J=1.65, 8.91 Hz, 2H), 8.02 (d, J=8.91 Hz, 2H), 8.34 (d, J=1.65 Hz, 2H), 10.10 (s, 2H)

(8) Synthesis of (S)-6,6'-divinyl-2,2'-bis(tert-butyldimethylsilyloxy)-1,1'-binaphthyl In 60 ml of ether were dissolved 3.05 g (5.34 mmol) of (S)-6,6'-diformyl-2,2'-bis(tert-butyldimethylsilyloxy)-1,1'-binaphthyl and 5.73 g (16.0 mmol) of triphenylmethylphosphonium bromide. Thereto was added 1.80 g (16.0 mmol) of potassium t-butoxide. This mixture was stirred at room temperature for 4 hours. Water was added to the reaction mixture, and the resultant mixture was subjected to liquid separation. The organic layer was washed with saturated sodium chloride solution and water and then dried with anhydrous magnesium sulfate. The dried organic layer was concentrated for solvent removal, and the residue was purified by silica gel column chromatography (hexane/ethyl acetate=6/1 by volume). As a result, 2.87 g (yield, 95%) of the target compound was obtained.

$^1$H NMR (CDCl$_3$) δ−0.21 (s, 6H), 0.02 (s, 6H), 0.50 (s, 18H), 5.23 (dd, J=0.99, 10.89 Hz, 2H), 5.75 (dd, J=0.99, 17.48 Hz, 2H), 6.83 (dd, J=10.89 17.48 Hz, 2H), 7.12–7.18 (m, 4H), 7.36 (dd, J=1.65, 8.91 Hz, 2H), 7.73 (d, J=1.28 Hz, 2H), 7.78 (d, J=8.91 Hz, 2H)

(9) Synthesis of (S)-6,6'-divinyl-2,2'-dihydroxy-1,1'-binaphthyl

In 50 ml of tetrahydrofuran was dissolved 2.87 g (5.06 mmol) of (S)-6,6'-diformyl-2,2'-bis(tert-butyldimethylsilyloxy)-1,1'-binaphthyl. Thereto was added 5 ml of water, followed by a tetrahydrofuran solution of tetramethylammonium fluoride (5.1 mmol). This mixture was stirred at room temperature for 4 hours and then extracted with ether. The organic layer obtained was dried with anhydrous magnesium sulfate. The dried organic layer was concentrated for solvent removal, and the residue was purified by silica gel column chromatography (hexane/ethyl acetate=1/1 by volume). As a result, 0.77 g (yield, 45%) of the target compound was obtained.

$^1$H NMR (CDCl$_3$) δ5.01 (s, 2H), 5.28 (d, J=10.89 Hz, 2H), 5.78 (d, J=17.48 Hz, 2H), 6.84 (dd, J=10.89, 17.48 Hz, 2H), 7.11 (d, J=8.91 2H), 7.37 (d, J=8.91 Hz, 2H), 7.46 (dd, J=1.65, 8.91 Hz, 2H), 7.82 (d, J=1.32 Hz, 2H), 7.96 (d, J=8.91 Hz, 2H)

(10) Synthesis of (R)-2'-diphenylphosphino-1,1'-binaphthalen-2-yloxy[(S)-6,6'-divinyl-1,1'-binaphthalene-2,2'-diyloxy]phosphine In 6 ml of ether were dissolved 0.11 g (0.24 mmol) of (R)-2'-diphenylphosphino-2-hydroxy-1,1'-binaphthyl and 0.16 g (0.35 mmol) of (S)-6,6'-divinyl-1,1'-binaphthalene-2,2'-dioxychlorophosphine. Thereto were added dropwise at 0° C. 0.06 ml (0.43 mmol) of triethylamine solution and 2 ml of ether. This mixture was stirred at that temperature for 1 hour and then at room temperature for 24 hours. Ice water was added to the reaction mixture, and the resultant mixture was subjected to liquid separation. Thereafter, the aqueous layer was extracted with ether, and the resultant organic layer was dried with anhydrous magnesium sulfate. The dried organic layer was concentrated for solvent removal, and the residue was purified by silica gel column chromatography (hexane/methylene chloride=2/1 to 1/1 by volume). As a result, 0.13 g (yield, 68%) of the target compound was obtained.

$^1$H NMR (CDCl$_3$) δ5.30 (m, 2H), 5.80 (m, 2H), 6.02 (d, J=8.90 Hz, 1H), 6.70–8.05 (m, 33H)

$^{31}$P NMR (CDCl$_3$) δ145.1 (d, J=30.5 Hz), −13.3 (d, J=30.5)

EXAMPLE 2

Synthesis of (R)-2'-diphenylphosphino-6-vinyl-1,1'-binaphthalen-2-yloxy[(S)-6,6'-divinyl-1,1'-binaphthalene-2,2'-diyloxy]phosphine (1) Synthesis of (R)-2,2'-bis[trifluoromethanesulfonyloxy]-1,1'-binaphthyl In 181 ml of methylene chloride were dissolved 36.2 g (127 mmol) of (R)-binaphthol and 25.2 g (319 mmol) of pyridine. This solution was cooled to 0° C. Thereto was added dropwise 76.5 ml (271 mmol) of an anhydrous triflate. Thereafter, the resultant mixture was stirred at room temperature for 18 hours, and 200 ml of 2 N hydrochloric acid was then added to the reaction mixture to wash the same. The organic layer was washed with water and a sodium chloride solution, and the solvent was then distilled off, whereby 69.3 g of a crude reaction product was obtained. The crude product was recrystallized from 280 ml of hexane to obtain 64.1 g (yield, 92%) of the target compound.

$^1$H NMR (CDCl$_3$) δ7.25–8.15 (m, aromatic)

(2) Synthesis of (R)-2'-diphenylphosphinyl-2-[trifluoromethanesulfonyloxy]-1,1'-binaphthyl In 100 ml of dimethyl sulfoxide were dissolved 11 g (20 mmol) of (R)-2,2'-bis[trifluoromethanesulfonyloxy]-1,1'-binaphthyl, 0.225 g (50 mol %) of palladium acetate, and 0.43 g (50 mol %) of 1,3-bis(diphenylphosphino)propane. This solution was stirred at room temperature for 1.5 hours. Thereto was added a solution prepared by dissolving 8.08 g (40 mmol) of diphenylphosphine oxide and 20 ml of diisopropylethylamine in 100 ml of dimethyl sulfoxide. The resultant mixture was stirred at 100° C. for 12 hours. After the reaction mixture was cooled to room temperature, 75 ml of methylene chloride was added thereto. This solution was cooled in an ice bath, and 100 ml of 2 N hydrochloric acid was gradually added dropwise thereto. The resultant mixture was stirred at room temperature for 30 minutes and then subjected to liquid separation. The aqueous layer was extracted with methylene chloride. The resultant organic layer was collected, washed with water, and then dried with magnesium sulfate. The dried organic layer was concentrated for solvent removal, and the residue was purified by silica gel column chromatography (hexane/ethyl acetate=4/1 to 1/4 by volume). As a result, 11.5 g (yield, 96%) of the target compound was obtained as yellowish white crystals.

$[\alpha]_D^{24}$ 44.45° (c 0.50, CHCl$_3$)

$^1$H NMR (CDCl$_3$) δ7.0–8.01 (m, aromatic)

$^{31}$P NMR (CDCl$_3$) δ28.73 (s)

(3) Synthesis of (R)-2'-diphenylphosphinyl-2-hydroxy-1,1'-binaphthyl

To 11.5 g (19.2 mmol) of (R)-2'-diphenylphosphinyl-2-[trifluoromethanesulfonyloxy]-1,1'-binaphthyl were added 2.42 g (57.6 mmol) of lithium hydroxide monohydrate, tetrahydrofuran (75 ml), and purified water (25 ml). This mixture was stirred overnight. The tetrahydrofuran was distilled off at a reduced pressure, and toluene (30 ml) and 2 N hydrochloric acid (50 ml) were added. After the resultant mixture was stirred and then subjected to liquid separation, the organic layer was dried with anhydrous magnesium sulfate. The solvent was then distilled off to obtain 9.03 g (yield, 100%) of the target compound.

(4) Synthesis of (R)-6-bromo-2'-diphenylphosphinyl-2-hydroxy-1,1'-binaphthyl

In 150 ml of dioxane was dissolved 4 g (8.49 mmol) of (R)-2'-diphenylphosphinyl-2-hydroxy-1,1'-binaphthyl. Thereto was added dropwise at 5° C. a solution of 1.75 ml (34 mmol) of bromine in 20 ml of dioxane. After this mixture was stirred at room temperature for 2 hours, it was neutralized with an aqueous sodium thiosulfate solution and then extracted with chloroform. The resultant organic layer was washed with saturated sodium chloride solution and then dried with anhydrous magnesium sulfate. The solvent was distilled off at a reduced pressure to obtain a yellow solid, which was purified by silica gel column chromatography (methylene chloride/ethyl acetate=1/1 by volume). As a result, 4.06 g (yield, 87%) of the target compound was obtained.

$^1$H NMR (CDCl$_3$) δ9.05 (bs, 1H), 7.95–7.17 (m, 2H), 7.65–7.53 (m, 7H), 7.42–7.32 (m, 2H), 7.26–7.17 (m, 2H), 7.06–6.88 (m, 3H), 6.81–6.72 (m, 2H), 6.27 (d, J=8.91, 1H)

$^{31}$P NMR (CDCl$_3$) δ31.26 (s)

(5) Synthesis of (R)-6-bromo-2'-diphenylphosphino-2-hydroxy-1,1'-binaphthyl

In 40 ml of xylene was dissolved 3.09 g (5.63 mmol) of (R)-6-bromo-2'-diphenylphosphinyl-2-hydroxy-1,1'-binaphthyl. Thereto was added 15.7 ml (112 mmol) of triethylamine, followed by 5.7 ml (56.4 mmol) of trichlorosilane. The resultant mixture was stirred at 110° C. for 22 hours. Saturated aqueous sodium bicarbonate solution was added thereto to terminate the reaction. Thereafter, the reaction mixture was filtered to remove the salt, washed with toluene, and then subjected to liquid separation. The organic layer was dried with anhydrous magnesium sulfate, and the solvent was distilled off. The residue was purified by silica gel column chromatography (chloroform). As a result, 1.94 g (yield, 65%) of the target compound was obtained.

$^1$H NMR (CDCl$_3$) δ7.96–7.80 (m, 4H), 7.52–7.43 (m, 2H), 7.33–6.98 (m, 14H), 6.55 (d, J=8.91, 1H), 4.62 (s, 1H)

$^{31}$P NMR (CDCl$_3$) δ–12.82 (s)

(6) Synthesis of (R)-2'-diphenylphosphino-2-hydroxy-6-vinyl-1,1'-binaphthyl

In 12 ml of dimethylformamide were dissolved 1.0 g (1.88 mmol) of (R)-6-bromo-2'-diphenylphosphino-2-hydroxy-1,1'-binaphthyl, 210 mg (0.182 mmol) of Pd(PPh$_3$)$_4$, 0.4 ml (2.87 mmol) of 2-vinyl-5,5-dimethyl-1,2-dioxa-3-borinane, and 0.965 g (4.54 mmol) of tripotassium phosphate monohydrate. This solution was stirred at 80° C. for 16 hours. The reaction mixture was diluted with water and then extracted with diethyl ether. The resultant organic layer was washed with saturated sodium chloride solution and then dried with anhydrous magnesium sulfate. The solvent was distilled off, and the residue was purified by silica gel column chromatography (chloroform). As a result, 618 mg (yield, 68%) of the target compound was obtained.

$^1$H NMR (CDCl$_3$) δ7.95–7.86 (m, 3H), 7.72 (bs, 1H), 7.54–7.01 (m, 1H), 6.79 (dd, J=17.15, 10.55, 1H), 6.69 (d, J=8.91 Hz, 1H), 5.7 (d, J=17.15, 1H), 5.22 (d, J=10.55, 1H), 4.53 (s, 1H)

$^{31}$P NMR (CDCl$_3$) δ–13.01 (s)

(7) Synthesis of (R)-2'-diphenylphosphino-6-vinyl-1,1'-binaphthalen-2-yloxy[(S)-6,6'-divinyl-1,1'-binaphthalene-2,2'-diyloxy]phosphine In 20 ml of ether were dissolved 0.45 g (0.936 mmol) of (R)-2'-diphenylphosphino-2-hydroxy-6-vinyl-1,1'-binaphthyl and (S)-6,6'-divinyl-1,1'-binaphthylene-2,2'-dioxychlorophosphine (1.03 mmol). The solution was cooled to 0° C., and 0.2 ml (1.44 mmol) of triethylamine was added thereto. This mixture was stirred at room temperature for 24 hours. Ice water was then added thereto to terminate the reaction, and the resultant mixture was subjected to liquid separation. Thereafter, the aqueous layer was extracted with ether, and the resultant organic layer was dried with magnesium sulfate. The solvent was distilled off, and the residue was purified by silica gel column chromatography (hexane/methylene chloride=1/1 by volume). As a result, 302 mg (yield, 38%) of the target compound was obtained.

$^1$H NMR (CDCl$_3$) δ8.06–6.60 (m, 33H), 6.00 (d, J=8.91 Hz, 1H), 5.84–5.23 (m, 6H)

$^{31}$P NMR (CDCl$_3$) δ146.0 (d, J=30.5 Hz), –13.2 (d, J=30.5 Hz)

EXAMPLE 3

(1) Suspension Copolymerization

To 0.4% aqueous poly(vinyl alcohol) solution was added, with sufficient stirring at 80° C., a solution prepared by dissolving 100 mg (0.122 mmol) of (R)-2'-diphenylphosphino-1,1'-binaphthalen-2-yloxy[(S)-6,6'-divinyl-1,1'-binaphthalene-2,2'-diyloxy]phosphine, 0.45 ml (3.93 mmol) of styrene, 0.035 ml (0.135 mmol) of divinylbenzene, and 20.2 mg (0.0813 mmol) of 2,2'-azobis (2,4-dimethylvaleronitrile) (hereinafter abbreviated as V-65) in 0.75 ml of toluene. The reaction mixture was stirred for 24 hours at a rotational speed of 400 rpm. The polymerization product obtained was taken out by filtration, washed with water and methanol, and then dried at a reduced pressure to obtain a polymer as a light-yellow solid.

(2) Solution Copolymerization in Chloroform

Into a 20-ml Schlenk tube were introduced 100 mg (0.122 mmol) of (R)-2'-diphenylphosphino-1,1'-binaphthalen-2-yloxy[(S)-6,6'-divinyl-1,1'-binaphthalene-2,2'-diyloxy] phosphine, 0.42 ml (3.66 mmol) of styrene, 0.11 ml (0.424 mmol) of divinylbenzene, 20.1 mg (0.081 mmol) of V-65, and 1.5 ml of chloroform. The contents were heated at 70° C. for 5 hours. Methanol was added to the reaction mixture which had solidified. As a result, a white precipitate generated. The precipitate was taken out by filtration, washed with methanol and toluene, and then dried at a reduced pressure to obtain a polymer as a light-yellow solid.

(3) Solution Copolymerization in Toluene

Into a 20-ml Schlenk tube were introduced 100 mg (0.122 mmol) of (R)-2'-diphenylphosphino-1,1'-binaphthalen-2-yloxy[(S)-6,6'-divinyl-1,1'-binaphthalene-2,2'-diyloxy] phosphine, 0.42 ml (3.66 mmol) of styrene, 0.11 ml (0.424 mmol) of divinylbenzene, 20.1 mg (0.081 mmol) of V-65, and 1.5 ml of toluene. The contents were heated at 70° C. for 5 hours. Methanol was added to the reaction mixture which had solidified. As a result, a white precipitate generated. The precipitate was taken out by filtration, washed with methanol and toluene, and then dried at a reduced pressure to obtain a polymer as a light-yellow solid.

(4) Solution Copolymerization in Toluene

Into a 20-ml Schlenk tube were introduced 50 mg (0.061 mmol) of (R)-2'-diphenylphosphino-1,1'-binaphthalen-2-yloxy[(S)-6,6'-divinyl-1,1'-binaphthalene-2,2'-diyloxy] phosphine, 0.27 ml (2.03 mmol) of divinylbenzene, 5.2 mg (0.021 mmol) of V-65, and 0.5 ml of toluene. The contents were heated at 80° C. for 14 hours. MeOH was added to the reaction mixture which had solidified, and the resultant precipitate was taken out by filtration, washed with MeOH, and then dried at a reduced pressure to obtain a polymer as a light-yellow solid.

EXAMPLE 4

Reaction of Polymer with Rhodium Dicarbonylacetylacetonate

Into a 20-ml Schlenk tube were introduced 4.1 mg (0.0159 mmol) of Rh(acac)(CO)$_2$, 304 mg of the polymer obtained in Example 3 (4) (containing 0.059 mmol in terms of monomer amount), and 5 ml of benzene. The contents were stirred with heating at room temperature for 2 hours. The reaction mixture was freeze-dried to obtain a reaction product as a yellowish orange solid.

EXAMPLE 5

Asymmetric Hydroformylation of Styrene

Into a 50-ml stainless-steel autoclave were introduced 61 mg of the rhodium complex synthesized in Example 4 (containing 0.0031 mmol of rhodium), 0.71 ml (6.20 mmol) of styrene, and 0.35 ml of benzene. The contents were stirred at 60° C. for 12 hours in an atmosphere of 10 atm carbon monoxide and 10 atm hydrogen. A small portion of the reaction mixture was taken out and filtered to remove the catalyst. This reaction mixture was analyzed by $^1$H NMR spectrometry to determine the conversion. As a result, the conversion was found to be 99%. The proportion of the α-methylphenylacetaldehyde to dihydrocinnamaldehyde yielded (regioselectivity) was 89:11. These reaction products were converted to carboxylic acids by Jones oxidation, and then analyzed by GC using a chiral column (Chrompack Cp-Cyclodex β-236M) to determine the enantiomer excess. As a result, the enantiomer excess was found to be 89% ee.

EXAMPLE 6

Reuse of Catalyst

Into a 50-ml pressure bottle made of glass were introduced 63 mg of the rhodium complex synthesized in Example 4 (containing 0.0031 mmol of rhodium), 0.71 ml (6.20 mmol) of styrene, and 0.35 ml of benzene. The contents were stirred at 60° C. for 3 hours in an atmosphere of 2.5 atm carbon monoxide and 2.5 atm hydrogen. As a result, the conversion was 41%, the regioselectivity was 88:12, and the enantiomer excess was 86% ee. After completion of the reaction, the benzene solution supernatant containing the reaction products and substrate was taken out with a syringe in an argon atmosphere. After the residue was washed with benzene, 0.71 ml (6.20 mmol) of styrene and 0.35 ml of benzene were added thereto to conduct a catalytic reaction in the same manner. As a result, the conversion in this reaction was 48%, the regioselectivity was 90:10, and the enantiomer excess was 86% ee.

EXAMPLE 7

(1) Suspension Copolymerization

To 0.4% aqueous poly(vinyl alcohol) solution was added, with sufficient stirring at 80° C., a solution prepared by dissolving 100 mg (0.122 mmol) of (R)-2'-diphenylphosphino-6-vinyl-1,1'-binaphthalen-2-yloxy[(S)-6,6'-divinyl-1,1'-binaphthalene-2,2'-diyloxy]phosphine, 0.45 ml (3.93 mmol) of styrene, 0.035 ml (0.135 mmol) of divinylbenzene, and 20.2 mg (0.0813 mmol) of 2,2'-azobis (2,4-dimethylvaleronitrile) (hereinafter abbreviated as V-65) in 0.75 ml of toluene. The reaction mixture was stirred for 24 hours at a rotational speed of 400 rpm. The polymerization product obtained was taken out by filtration, washed with water and methanol, and then dried at a reduced pressure to obtain a polymer as a light-yellow solid.

(2) Solution Copolymerization in Chloroform

Into a 20-ml Schlenk tube were introduced 100 mg (0.122 mmol) of (R)-2'-diphenylphosphino-6-vinyl-1,1'-binaphthalen-2-yloxy[(S)-6,6'-divinyl-1,1'-binaphthalene-2,2'-diyloxy]phosphine, 0.42 ml (3.66 mmol) of styrene, 0.11 ml (0.424 mmol) of divinylbenzene, 20.1 mg (0.081 mmol) of V-65, and 1.5 ml of chloroform. The contents were heated at 70° C. for 5 hours. Methanol was added to the reaction mixture which had solidified. As a result, a white precipitate generated. The precipitate was taken out by filtration, washed with methanol and toluene, and then dried at a reduced pressure to obtain a polymer as a light-yellow solid.

(3) Solution Copolymerization in Toluene

Into a 20-ml Schlenk tube were introduced 100 mg (0.122 mmol) of (R)-2'-diphenylphosphino-6-vinyl-1,1'-binaphthalen-2-yloxy[(S)-6,6'-divinyl-1,1'-binaphthalene-2,2'-diyloxy]phosphine, 0.42 ml (3.66 mmol) of styrene, 0.11 ml (0.424 mmol) of divinylbenzene, 20.1 mg (0.081 mmol) of V-65, and 1.5 ml of toluene. The contents were heated at 70° C. for 5 hours. Methanol was added to the reaction mixture which had solidified. As a result, a white precipitate generated. The precipitate was taken out by filtration, washed with methanol and toluene, and then dried at a reduced pressure to obtain a polymer as a light-yellow solid.

EXAMPLE 8

Reaction of Polymer with Rhodium Dicarbonylacetylacetonate

Into a 20-ml Schlenk tube were introduced 4.1 mg (0.0159 mmol) of Rh(acac)(CO)$_2$, 304 mg of the polymer obtained in Example 7 (containing 0.059 mmol in terms of monomer amount), and 5 ml of benzene. The contents were stirred with heating at room temperature for 2 hours. The reaction mixture was freeze-dried to obtain a reaction product as a yellowish orange solid.

EXAMPLE 9

Asymmetric Hydroformylation of Styrene

Into a 50-ml stainless-steel autoclave were introduced 61 mg of the rhodium complex synthesized in Example 8 (containing 0.0031 mmol of rhodium), 0.71 ml (6.20 mmol) of styrene, and 0.35 ml of benzene. The contents were stirred at 60° C. for 12 hours in an atmosphere of 10 atm carbon monoxide and 10 atm hydrogen. A small portion of the reaction mixture was taken out and filtered to remove the catalyst. This reaction mixture was analyzed by $^1$H NMR spectrometry to determine the conversion. As a result, the conversion was found to be 99%. The proportion of the α-methylphenylacetaldehyde to dihydrocinnamaldehyde yielded (regioselectivity) was 89:11. These reaction products were converted to carboxylic acids by Jones oxidation, and then analyzed by GC using a chiral column (Chrompack Cp-Cyclodex β-236M) to determine the enantiomer excess. As a result, the enantiomer excess was found to be 89% ee.

While the invention has been described in detail and with reference to specific embodiments thereof, it will be apparent to one skilled in the art that various changes and modifications can be made therein without departing from the spirit and scope thereof.

What is claimed is:

1. A transition metal complex obtained by causing a transition metal compound to act on the polymer having structural units derived from a 2'-diarylphosphino-1,1-biphenylen-2-yloxy(6,6'-divinyl-1,1'-binaphthalene-2, 2'diyloxy)phosphine derivative which is represented by the following general formula (III)

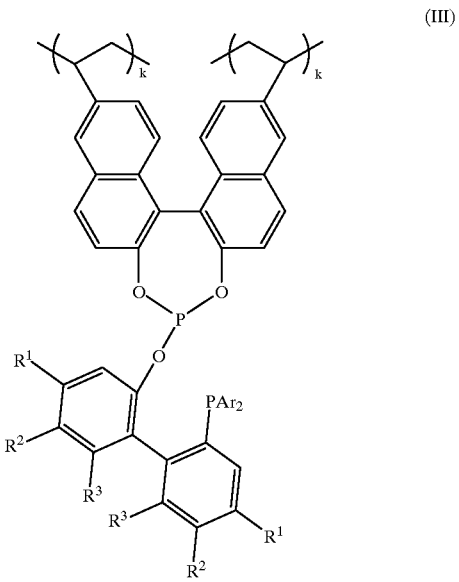

(III)

wherein Ar is an optionally substituted phenyl group or an optionally substituted naphthyl group; $R^1$ and $R^2$ each independently is a hydrogen atom, a lower alkyl group, a halogen atom, a hydrogen substituted lower alkyl group, or a benzyloxy group; $R^3$ is a lower alkyl group, a lower alkoxy group, a halogen atom, a halogen substituted lower alkyl group, or a benzyloxy group; provided that $R^2$ and $R^3$ may be bonded to each other to form a hydrocarbon ring, which may have one or more substituents selected from lower alkyl groups, halogen atoms, lower alkoxy groups, halogenated lower alkoxy groups, benzyloxy group, and vinyl group; and k is an integer of 2 to 100.

2. A transition metal complex obtained by causing a transition metal compound to act on the polymer having structural units

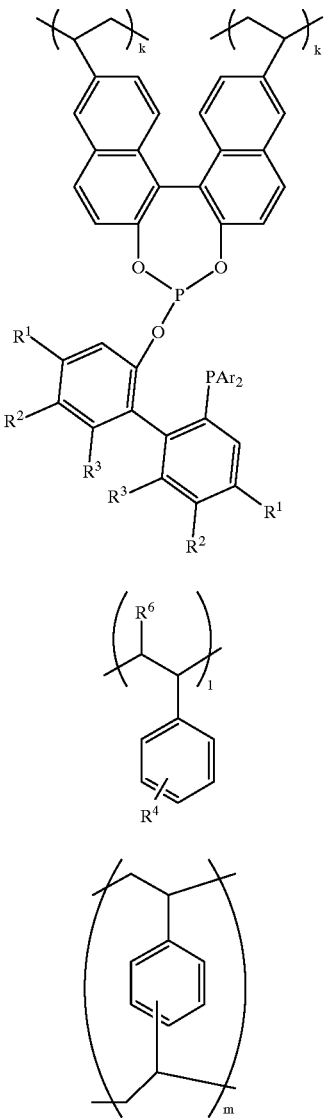

wherein Ar is an optionally substituted phenyl group or an optionally substituted naphthyl group; $R^1$ and $R^2$ each independently is a hydrogen atom, a lower alkyl group, a lower alkoxy group, a halogen atom, a halogen-substituted lower alkyl group, or a benzyloxy group; $R^3$ is a lower alkyl group, a lower alkoxy group, a halogen atom, a halogen-substituted lower alkyl group, or a benzyloxy group; provided that $R^2$ and $R^3$ may be bonded to each other to form a hydrocarbon ring, which may have one or more substituents selected from lower alkyl groups, halogen atoms, lower alkoxy groups, halogenated lower alkyl groups, a benzyloxy group, and a vinyl group; $R^4$ is a hydrogen atom, a lower alkyl group, a lower alkoxy group, or a halogen atom; $R^6$ is a hydrogen atom, or a methyl group; k is an integer of 2 to 100; and l and m each is an integer of 0 to 1,000; provided that at least one of l and m is not 0 and (k+l+m) is from 10 to 1,000.

3. The transition metal complex of claim 1, which has structural units derived from a compound which are represented by the following general formula (VI):

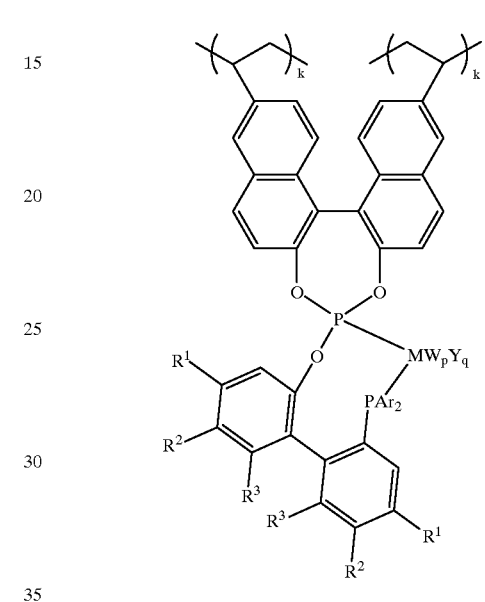

wherein Ar is an optionally substituted phenyl group or an optionally substituted naphthyl group; $R^1$ and $R^2$ each independently is a hydrogen atom, a lower alkyl group, a lower alkoxy group, a halogen atom, a halogen-substituted lower alkyl group, or a benzyloxy group; $R^3$ is a lower alkyl group, a lower alkoxy group, a halogen atom, a halogen-substituted lower alkyl group, or a benzyloxy group; provided that $R^2$ and $R^3$ may be bonded to each other to form a hydrocarbon ring, which may have one or more substituents selected from lower alkyl groups, halogen atoms, lower alkoxy groups, halogenated lower alkyl groups, a benzyloxy group, and a vinyl group; M is rhodium, iridium, palladium, or platinum; W is 1,5-cyclooctadiene, norbornadiene, a halogen atom, CO, acetoxy, allyl, or acetylacetonato; Y is a hydrogen atom, a halogen atom, $ClO_4$, $BF_4$, $PF_6$, $BPh_4$, $SnCl_2$, or $SnCl_3$; p and q each is 0 to 2, provided that at least one of p and q is not 0; and k is an integer of 2 to 100.

4. The transition metal complex of claim 2, which has structural units derived from compounds, said units being represented by the following general formulae (VI), (IV), and (V):

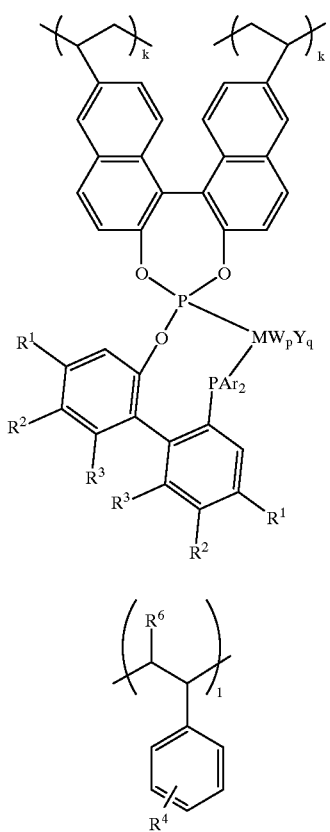

(IV)

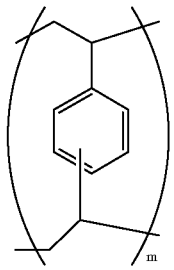

(VI)

(V)

wherein Ar is an optionally substituted phenyl group or an optionally substituted naphthyl group; $R^1$ and $R^2$ each independently is a hydrogen atom, a lower alkyl group, a lower alkoxy group, a halogen atom, a halogen-substituted lower alkyl group, or a benzyloxy group; $R^3$ is a lower alkyl group, a lower alkoxy group, a halogen atom, a halogen-substituted lower alkyl group, or a benzyloxy group; provided that $R^2$ and $R^3$ may be bonded to each other to form a hydrocarbon ring, which may have one or more substituents selected from lower alkyl groups, halogen atoms, lower alkoxy groups, halogenated lower alkyl groups, a benzyloxy group, and a vinyl group; $R^4$ is a hydrogen atom, a lower alkyl group, a lower alkoxy group, or a halogen atom; $R^6$ is a hydrogen atom or a methyl group; M is rhodium, iridium, palladium, or platinum; W is 1,5-cyclooctadiene, norbornadiene, a halogen atom, CO, acetoxy, allyl, or acetylacetonato; Y is a hydrogen atom, a halogen atom, $ClO_4$, $BF_4$, $PF_6$, $BPh_4$, $SnCl_2$, or $SnCl_3$; p and q each is 0 to 2, provided that at least one of p and q is not 0; k is an integer of 2 to 100; and l and m each is an integer of 0 to 1,000; provided that at least one of l and m is not 0 and (k+l+m) is from 10 to 1,000.

* * * * *